(12) United States Patent
Work et al.

(10) Patent No.: US 12,214,146 B2
(45) Date of Patent: Feb. 4, 2025

(54) CONTROLLED RELEASE OF A HYDROPHILIC AGENT FROM A COATED SURFACE

(71) Applicant: Biocoat, Incorporated, Horsham, PA (US)

(72) Inventors: William James Work, Perkiomenville, PA (US); Raymond Joseph Gould, Thorndale, PA (US); Dhruv Patel, Colmar, PA (US); Robert W Hergenrother, Huntingdon Valley, PA (US)

(73) Assignee: Biocoat, Incorporated, Horsham, PA (US)

( * ) Notice: Subject to any disclaimer, the term of this patent is extended or adjusted under 35 U.S.C. 154(b) by 1035 days.

(21) Appl. No.: 17/118,143

(22) Filed: Dec. 10, 2020

(65) Prior Publication Data

US 2021/0178129 A1 Jun. 17, 2021

Related U.S. Application Data

(60) Provisional application No. 62/946,523, filed on Dec. 11, 2019.

(51) Int. Cl.
*A61M 25/10* (2013.01)
*A61K 31/145* (2006.01)
(Continued)

(52) U.S. Cl.
CPC ........... *A61M 25/10* (2013.01); *A61K 31/145* (2013.01); *A61K 31/155* (2013.01);
(Continued)

(58) Field of Classification Search
CPC ... A61M 25/10; A61K 31/145; A61K 31/155; A61K 31/165; A61K 31/166;
(Continued)

(56) References Cited

U.S. PATENT DOCUMENTS

| 2,999,056 A | 9/1961 | Tanner |
| 4,349,467 A | 9/1982 | Williams et al. |

(Continued)

FOREIGN PATENT DOCUMENTS

| CN | 1889982 A | 1/2007 |
| CN | 1950116 A | 4/2007 |

(Continued)

OTHER PUBLICATIONS

Frech et al., "A Simple Noninvasive Technique to Test Nonthrombogenic Surfaces," The American Journal of Roentgenology, vol. 113 (1971), p. 765-768.

(Continued)

*Primary Examiner* — Lauren P Farrar
(74) *Attorney, Agent, or Firm* — BakerHostetler (57) ABSTRACT

The present invention is an implantable medical device comprising (i) a base coat layer having an inner and outer surface, the inner surface of the base coat layer contacting the implantable medical device; (ii) a top-coat layer of a hydrophilic polymer chemically crosslinked and covalently bonded to the outer surface of the base coat layer, the hydrophilic polymer comprising an anionic polyelectrolyte; and (iii) an amount of a hydrophilic cationic drug agent added to the top-coat layer sufficient to provide an effective dosage of the drug agent for delivery to a patient, whereby the hydrophilic cationic drug agent is initially adsorbed into the anionic polyelectrolyte of the top-coat layer and the hydrophilic cationic drug agent having a release rate after the medical device is implanted within a patient's body.

30 Claims, 2 Drawing Sheets

(51) Int. Cl.
- *A61K 31/155* (2006.01)
- *A61K 31/165* (2006.01)
- *A61K 31/166* (2006.01)
- *A61K 31/167* (2006.01)
- *A61K 31/437* (2006.01)
- *A61K 31/4409* (2006.01)
- *A61K 31/473* (2006.01)
- *A61K 31/502* (2006.01)
- *A61K 31/505* (2006.01)
- *A61K 31/506* (2006.01)
- *A61K 31/52* (2006.01)
- *A61K 31/53* (2006.01)
- *A61K 31/5377* (2006.01)
- *A61K 31/655* (2006.01)
- *A61K 31/7008* (2006.01)
- *A61K 31/7048* (2006.01)
- *A61K 31/7076* (2006.01)
- *A61K 31/708* (2006.01)
- *A61L 29/08* (2006.01)
- *A61L 29/16* (2006.01)
- *B05D 5/00* (2006.01)
- *B05D 7/00* (2006.01)

(52) U.S. Cl.
CPC .......... *A61K 31/165* (2013.01); *A61K 31/166* (2013.01); *A61K 31/167* (2013.01); *A61K 31/437* (2013.01); *A61K 31/4409* (2013.01); *A61K 31/473* (2013.01); *A61K 31/502* (2013.01); *A61K 31/505* (2013.01); *A61K 31/506* (2013.01); *A61K 31/52* (2013.01); *A61K 31/53* (2013.01); *A61K 31/5377* (2013.01); *A61K 31/655* (2013.01); *A61K 31/7008* (2013.01); *A61K 31/7048* (2013.01); *A61K 31/7076* (2013.01); *A61K 31/708* (2013.01); *A61L 29/085* (2013.01); *A61L 29/16* (2013.01); *B05D 5/00* (2013.01); *B05D 7/542* (2013.01); *B05D 7/544* (2013.01); *A61L 2300/204* (2013.01); *A61L 2300/206* (2013.01); *A61L 2300/208* (2013.01); *A61L 2300/21* (2013.01); *A61L 2300/216* (2013.01); *A61L 2300/232* (2013.01); *A61L 2300/402* (2013.01); *A61L 2300/404* (2013.01); *A61L 2300/406* (2013.01); *A61L 2300/41* (2013.01); *A61L 2300/416* (2013.01); *A61L 2300/442* (2013.01); *A61L 2420/02* (2013.01); *A61L 2420/08* (2013.01); *A61M 2025/105* (2013.01); *A61M 2207/00* (2013.01)

(58) Field of Classification Search
CPC ............... A61K 31/167; A61K 31/437; A61K 31/4409; A61K 31/473; A61K 31/502; A61K 31/505; A61K 31/506; A61K 31/52; A61K 31/53; A61K 31/5377; A61K 31/655; A61K 31/7008; A61K 31/7048; A61K 31/7076; A61K 31/708; A61L 29/085; A61L 29/16; A61L 2300/204; A61L 2300/206; A61L 2300/208; A61L 2300/21; A61L 2300/216; A61L 2420/02; A61L 2420/08; B05D 5/00; B05D 7/542; B05D 7/544
See application file for complete search history.

(56) References Cited

U.S. PATENT DOCUMENTS

| | | |
|---|---|---|
| 4,642,267 A | 2/1987 | Creasy et al. |
| 4,801,475 A | 1/1989 | Halpern et al. |
| 4,990,357 A | 2/1991 | Karakelle et al. |
| 5,002,582 A | 3/1991 | Guire et al. |
| 5,023,114 A | 6/1991 | Halpern et al. |
| 5,037,677 A | 8/1991 | Halpern et al. |
| 5,091,205 A | 2/1992 | Fan |
| 5,217,492 A | 6/1993 | Guire et al. |
| 5,443,455 A | 8/1995 | Hergenrother et al. |
| 5,509,899 A | 4/1996 | Fan et al. |
| 5,531,715 A | 7/1996 | Engelson et al. |
| 5,702,754 A | 12/1997 | Zhong |
| 5,749,837 A | 5/1998 | Palermo et al. |
| 5,789,018 A | 8/1998 | Engelson et al. |
| 6,048,620 A | 4/2000 | Zhong |
| 6,087,416 A | 7/2000 | Pearlstine et al. |
| 6,221,061 B1 | 4/2001 | Engelson et al. |
| 6,278,018 B1 | 8/2001 | Swan |
| 6,534,559 B1 | 3/2003 | Vanderlaan et al. |
| 6,558,798 B2 | 5/2003 | Zhong et al. |
| 6,673,453 B2 * | 1/2004 | Beavers ............... A61L 29/085 427/407.1 |
| 6,709,706 B2 | 3/2004 | Zhong et al. |
| 7,384,984 B2 | 6/2008 | Lewandowski |
| 7,550,444 B2 | 6/2009 | Stucke et al. |
| 8,163,327 B2 | 4/2012 | Finley |
| 8,318,263 B2 | 11/2012 | Carlson et al. |
| 8,541,498 B2 | 9/2013 | Sandhu et al. |
| 9,375,517 B2 | 6/2016 | Babcock |
| 9,737,639 B2 | 8/2017 | Babcock |
| 10,525,170 B2 | 1/2020 | Havenstrite et al. |
| 11,441,092 B2 | 9/2022 | Rhodes et al. |
| 11,634,656 B2 | 4/2023 | Zhu et al. |
| 2002/0037984 A1 | 3/2002 | Vanderbilt |
| 2002/0041899 A1 | 4/2002 | Chudzik et al. |
| 2005/0131148 A1 * | 6/2005 | Lewandowski ....... C08F 291/00 525/187 |
| 2007/0032882 A1 | 2/2007 | Lodhi et al. |
| 2007/0141365 A1 | 6/2007 | Jelle et al. |
| 2007/0286959 A1 | 12/2007 | Palmer |
| 2008/0206096 A1 | 8/2008 | Deka |
| 2008/0213334 A1 | 9/2008 | Lockwood et al. |
| 2009/0324684 A1 * | 12/2009 | Atanasoska ............. A61L 31/08 424/426 |
| 2010/0247599 A1 | 9/2010 | Kroehen et al. |
| 2011/0063567 A1 | 3/2011 | Domschke |
| 2011/0200828 A1 | 8/2011 | Li et al. |
| 2011/0134387 A1 | 9/2011 | Samuel et al. |
| 2012/0178872 A1 | 7/2012 | Blanquer et al. |
| 2013/0323291 A1 | 12/2013 | Li et al. |
| 2014/0004170 A1 * | 1/2014 | Krohen ................... A61L 31/10 427/2.24 |
| 2014/0193474 A1 | 7/2014 | Babcock et al. |
| 2017/0281831 A1 | 10/2017 | Militello |
| 2018/0244927 A1 | 8/2018 | Mccoy et al. |

FOREIGN PATENT DOCUMENTS

| | | |
|---|---|---|
| CN | 107206119 A | 9/2017 |
| CN | 108603136 A | 9/2018 |
| CN | 109966560 A | 7/2019 |
| EP | 0220919 A2 | 5/1987 |
| EP | 0379156 A2 | 7/1990 |
| EP | 0480809 A2 | 4/1992 |
| EP | 0669837 A1 | 9/1995 |
| EP | 0728487 A1 | 8/1996 |
| EP | 0790839 A1 | 8/1997 |
| EP | 0963761 A1 | 12/1999 |
| JP | 2004-520088 A | 7/2004 |
| JP | 2006176934 A | 7/2006 |
| JP | 2010090049 A | 4/2010 |
| JP | 2010126482 A | 6/2010 |
| JP | 2011046619 A | 3/2011 |
| JP | 2011046652 A | 3/2011 |
| TW | 287564 B | 10/2007 |
| WO | 9614885 A1 | 5/1996 |
| WO | 0078884 A1 | 12/2000 |
| WO | 2010041527 A | 4/2010 |
| WO | 2011125713 A1 | 3/2011 |

(56) References Cited

FOREIGN PATENT DOCUMENTS

| WO | 2010041530 A1 | 3/2012 |
| WO | 2014036498 A2 | 3/2014 |
| WO | 2018/237224 A1 | 12/2018 |

OTHER PUBLICATIONS

Ovitt et al., "Guidewire Thrombogenicity and Its Reduction", Radiology, vol. 111 (1974), p. 43-46.

Albarghouthi et al., "Poly-N-hydroxyethylacrylamide(polyDuramide): A novel, hydrophilic, self-coating polymer matrix for DNA sequencing by capillary electrophoresis", Electrophoresis, vol. 23 (2002), p. 1429-1440.

* cited by examiner

CONTROLLED RELEASE OF A HYDROPHILIC AGENT FROM A COATED SURFACE

CROSS-REFERENCE TO RELATED APPLICATION

This application claims priority to and the benefit of U.S. Provisional Patent Application No. 62/946,523, filed Dec. 11, 2019, the disclosure of which is incorporated herein by this reference in its entirety.

TECHNICAL FIELD

The present invention relates to the field of medical treatments involving the use of implantable medical devices for localized delivery of bioactive agents within a body, and more particularly, to a hydrophilic polymer coating for the surface of an implantable medical device that is formed from a charged polyelectrolyte with anionic functionality capable of adsorbing a cationic drug agent in a measured amount and providing a controlled release of the drug agent through the coating when delivered to a diseased or injured site within the body.

BACKGROUND OF THE INVENTION

The systemic administration of drug agents, such as by intravenous means, treats the body as a whole even though the disease to be treated may be localized. As an alternative medical approach, it has become common to treat a variety of problematic diseased conditions by introducing an implantable medical device having a biocompatible surface coating partly or completely into a body cavity to the site of the diseased condition, with such coated medical devices further bearing a therapeutic drug agent in order to target the drug delivery and treat the disease. For example, an implantable or insertable medical device, such as a stent or a balloon catheter, may be provided with a polymer matrix coating layer that contains a therapeutic agent, which upon placement of the medical device at a desired location within a patient, may be released from the polymer matrix and into specific tissue areas or organ parts, thereby achieving a desired therapeutic outcome. Using this type of targeted drug delivery through the mechanism of the coated intracorporeal medical device, a growing number of medical therapies are being effected by the application of a pharmaceutical or bioactive drug agent directly to the site where it is needed, thus avoiding the toxic concentration of drugs necessary to achieve proper dosing when the drug is administered systematically.

The successful implementation of targeted drug delivery using intracorporeal medical devices certainly rests on an applied coating firmly bonded to the underlying substrate, that is highly lubricious and biocompatible in nature in order to allow easy acceptance and passage of the device through the patient's body with little or no adverse reaction and/or effects on the internal vessels and organs by the intrusion of the foreign device. These characteristic features have been achieved with a high degree of success by a number of different hydrophilic coating preparations, one most notable being that described in U.S. Pat. No. 6,673,453, the description and associated teachings are incorporated herein by reference in their entirety. In the foregoing patent, biocompatible, lubricious, highly durable coatings for medical devices are produced and applied in a bi-laminar coating platform with a highly adherent base coat and a hydrophilic top-coat which is chemically grafted to the base coat. Primary among components used to formulate the top-coat is a charged polyelectrolyte polymer having an anionic functionality based on hyaluronic acid, a naturally occurring polysaccharide that is inherently biocompatible. The bilaminar coating is chemically crosslinked and covalently bonded for enhanced durability with low particulate count often required for demanding applications. The hyaluronic acid in the top-coat swells on hydration, which exhibits hydrogel behavior providing a coating layer that is extremely lubricious.

In recent years, a variety of polyelectrolyte hydrophilic coatings have begun to make advances in targeted drug delivery applications on the vehicle of implantable medical devices. Significant effort has been focused on the production of polyelectrolyte coatings that can initially adsorb a bioactive therapeutic agent so that it may be carried upon the coated device and then released over time from the coated surface of the implanted device when delivered to the implant site. Through modified formulations and adaptations of a "layer-by-layer" formation technique of polyelectrolyte coatings in alternating sequences of positive and negative layers crosslinked by their ionic interactions on the implantable devices, drug loading has been effected and time-release elution measured under in vivo conditions with some degree of consistency. Prior art examples of some of these more recently developed polyelectrolyte coatings for targeted delivery of bioactive, pharmaceutical drug agents are described in U.S. Pat. Publication Nos. 2008/0213334A1 (Polyelectrolyte Media for Bioactive Agent Delivery), 2010/0247599A1 (Drug-Releasing Polyelectrolyte Coating, Method of Forming, and Implantable Device), and 2014/0004170A1 (Coating of a Drug-Eluting Medical Device). Because chemical interactions between coatings and drugs are not always constant and reflect the functional groups, charges, and concentrations among the constituents, consistencies in the time-release and in the percentages of drug elution have been somewhat difficult to achieve, and while these and other prior art polyelectrolyte coatings, particularly those of the type formed "layer-by-layer", have been found to be effective in releasing drug agents, typically mixed into the layered coating, over an extended time measured in days, weeks and months, they have been far less effective, if at all satisfactory, in controlling the release of the drugs in a measured fashion over short spans measured in minutes as is being required by a growing number of advancing cardiovascular therapies, such as drug-coated balloons ("DCB") developed for the treatment of peripheral artery disease. Rather than a slow time-release of the drug agent, measured in days to months, in situ cardiovascular treatments like that of the DCB therapy, a far more rapid release is needed, sometimes over a span of minutes after the medical device is positioned at the site of the diseased artery. Because in the typical layer-by-layer polyelectrolyte coatings of the prior art, the drug agents are present as physical mixtures with the polymer so that drug elution depends upon the solubility of the drug in blood, the degree to which the carrier polymer swells in water, and the diffusion rate of the drug through the carrier polymer and any overlying polymer, the release rates achieved when consistent, are relatively slow and far too slow for effective treatment in those developing vascular therapies like DCB devices.

Accordingly, there is a need for an improved targeted drug delivery method for controlling the release of a bioactive pharmaceutical drug agent from the hydrophilic coated surface of an implanted medical device so that more rapid and consistent elution rates of the drug agent are achieved in situ at the intended treatment site.

SUMMARY OF THE INVENTION

Accordingly, it is a general purpose and object of the present invention to provide an improved targeted drug delivery method for controlling release of a bioactive pharmaceutical drug agent from a hydrophilic coated surface of an implanted medical device so that more rapid and consistent elution rates of the drug agent are achieved in situ at the intended treatment site.

A more particular object of the present invention is to provide an improved targeted drug delivery method using an implantable medical device having a polyelectrolyte hydrophilic coating capable of absorbing a measured amount of a pharmaceutically active drug agent and releasing the agent at a controlled rate necessary for proper treatment of a diseased condition when in place at the intended treatment site.

Another object of the present invention is to provide an improved method of employing a polyelectrolyte hydrophilic coating on the surface of an implantable medical device that is capable of incorporating the molecules of a bioactive drug into the coating for delivery to an intracorporeal treatment site and then effecting a controlled release of the drug molecules from the coating at the treatment site to interact with the body's tissues in specialized therapies.

Still another object of the present invention is to provide an improved option and alternative to layer-by-layer hydrophilic coatings used on medical devices to perform targeted drug deliveries within the body.

A still further object of the present invention is to provide an effective and reliable hydrophilic coating system for performing targeted drug deliveries on the surface of implantable medical devices to intracorporeal diseased sites for therapeutic treatment.

Briefly, these and other objects of the present invention are accomplished by an improved hydrophilic coating system and means for the controlled release of a hydrophilic cationic drug agent from a coated surface, such as that of an intracorporeal medical device, using a surface layer of a polyelectrolyte polymer coating having anionic functionality to initially adsorb the cationic drug and then gradually release that drug by ion exchange under the saline conditions typically found in tissues and blood. By cationic drug is meant any drug that, in water, either is cationic by its chemical nature or is protonated by water to become cationic.

The group of anionic polyelectrolytes that may be suitably employed in the present invention include sodium hyaluronate, hyaluronic acid, hyaluronan, poly(acrylic acid) homopolymer and copolymers, sodium alginate, heparin, carboxymethyl cellulose, methacrylic acid homopolymer and copolymers, maleic anhydride copolymers, itaconic acid copolymers, 2-acrylamido-2-methylpropane sulfonic acid copolymers, 3-Sulfopropyl acrylate copolymers. This adsorption and controlled release of the cationic drug agent through the anionic polyelectrolyte coating under saline conditions is particularly useful in effecting targeted drug deliveries in the performance of intravascular therapies.

For a better understanding of these and other aspects of the present invention, reference should be made to the following detailed description taken in conjunction with the accompanying drawings in which like reference numerals and character designate like parts throughout the figures thereof.

BRIEF DESCRIPTION OF THE DRAWINGS

The following is a brief description of the drawings.

DESCRIPTION OF THE INVENTION

The present invention implantable medical device comprising (i) a base coat layer having an inner and outer surface, the inner surface of the base coat layer contacting the implantable medical device; (ii) a top coat layer of a hydrophilic polymer chemically crosslinked and covalently bonded to the outer surface of the base coat layer, the hydrophilic polymer comprising an anionic polyelectrolyte; and (iii) an amount of a hydrophilic cationic drug agent added to the top coat layer sufficient to provide an effective dosage of the drug agent for delivery to a patient, whereby the hydrophilic cationic drug agent is initially adsorbed into the anionic polyelectrolyte of the top coat layer and the hydrophilic cationic drug agent having a release rate after the medical device is implanted within a patient's body. The invention also concerns method of making such devices.

It should be understood that the description further set forth herein is made for the purpose of illustrating the general principles of the invention but should not be taken in a limiting sense, the scope of the invention being best determined by reference to any associated claims.

In the described implementations of the present methodology of this case, some hydrophilic surface coatings applied to the substrate materials were derived and selectively constructed from those Coatings Appropriate for Medical Devices, described in U.S. Pat. No. 6,673,453 to Beavers, et al. for, which is incorporated herein in its entirety by reference. Such coatings, as described and taught in the incorporated patent, are applied in a bi-laminar coating platform with a highly adherent base coat and a hydrophilic top-coat which is chemically grafted to the base coat. Primary among components used to formulate the top-coat is a charged polyelectrolyte polymer having an anionic functionality based on hyaluronic acid, a naturally occurring polysaccharide that is inherently biocompatible. The hyaluronic acid in the top-coat swells on hydration which exhibits hydrogel behavior providing a coating layer that is extremely lubricious. In some embodiments, this bilaminar coating system commercially provided by Biocoat, Incorporated and available as HYDAK® coating compositions, includes a base coat initially applied to the substrate surface that firmly binds to the surface through a combination of hydrogen bonding and dipolar bonding, followed by application of a top coat that is chemically crosslinked and covalently bonded to the base coat to secure the bilaminar coating upon the substrate Some top coats employed in the present methodologies include those commercially available. One suitable top-coat is a polyelectrolyte polymer formulated from acrylic acid copolymerized with other hydrophilic monomers and mixed with additives to promote base coat wetting and bonding to the base coat. Another suitable top-coat is a polyelectrolyte polymer formulated from hyaluronic acid mixed with selected additives that promote base coat wetting, bonding of the top coat to the base coat and stabilizing the coating against hydrolytic degradation. Some base coats employed in the present methodologies include (i) acrylic copolymer (butyl acrylate, butyl methacrylate and acrylic acid) emulsion with polyaziridine crosslinker, as described in U.S. Pat. No. 6,673,453, and (ii) an acrylic polymer formulated from acrylic ester monomers, hydroxyethyl methacrylate, and monomers that promote bonding of the top coat to the base coat.

In some embodiments, the anionic polyelectrolyte of the top coat layer is selected from the group consisting of sodium hyaluronate, hyaluronic acid, hyaluronan, poly (acrylic acid) homopolymer and copolymers, sodium alginate, heparin, carboxymethyl cellulose, methacrylic acid homopolymer and copolymers, maleic anhydride copolymers, itaconic acid copolymers, 2-acrylamido-2-methylpropane sulfonic acid copolymers, and 3-sulfopropyl acrylate copolymers.

Preferred embodiments comprise a basecoat that contacts both a substrate and the top-coat composition. Some preferred basecoats are hydrophobic. In certain embodiments, the base coat layer comprises an acrylic polymer. Preferably, the base coat has cross-linking components that allow the top-coat to be cross-linked to the base coat.

Any suitable hydrophilic cationic drug agent may be utilized. In some embodiments, the hydrophilic cationic drug agent is selected from a group consisting of a class of water soluble, protonated amine drugs.

Suitable the hydrophilic cationic drug agent include anti-infectives, antibacterial, antifungal, antiarthritics, anti-inflammatories, photoactivatable naphthalimide dyes for tissue crosslinking, anesthetics, antiarrhythmics, antiprotozoal, antineoplastic, cancer treatments drugs and imiquimod.

In some embodiments, the anesthetics comprise one or more of Procaine hydrochloride (HCl), Benzocaine and Lidocaine HCl. One suitable antiarrhythmics comprises Procainamide HCl.

In certain embodiments, the antiprotozoals comprises one or more of Diminazene Aceturate and Pentamidine.

Antineoplastics include one or both of Improsulfan and Thiamiprine.

Suitable cancer treatments drugs include one or more of Tipiracil, Ponatinib hydrochloride, Radotinib hydrochloride, Alectinib hydrochloride, Copanlisib hydrochloride, Nelarabine, Tirapazamine, Clofarabine, Fludarabine, Vandetanib, and Abemaciclib.

In some embodiments, the anti-infectives comprise one or more of anti-bacterial, anti-viral, anti-fungal and anti-parasitic agents. In certain embodiments, the one or more of anti-bacterial, anti-viral, anti-fungal and anti-parasitic agents comprise aminoglycosides, cephalosporins, penicillins, chloramphenicol, isoniazid, trimethoprim and small cationic peptides or large peptides with polycationic domains. Antibacterial, antifungal, antiarthritics, anti-inflammatories may comprise streptomycin or animoglcoside.

The hydrophilic cationic drug agent may comprise one or more of Imiquimod, Tetracycline, Streptomycin, Niacinamide, Clindamycine, Dapsone, Naftifine, Miconazole, Erythromycin, Terbinafine, Amitriptyline, Bisoctrizole, Benzalkonium Chloride, Chlorhexidine, Celecoxib, N,N-Dimethyl 4-aminobenzene, Diclofenac, DOXepin, Fluconazole, Gabapentin, Ketamine, Lidocaine, Benzocaine, Metronida Zole, Morphine, Nicotine, Octenidine, and Octopirox.

In one embodiment, the hydrophilic cationic drug agent is a photoactive 4-amino substituted 1,8-naphthalamide compound.

In preferred embodiments, the amount of drug agent is sufficient for delivery to a targeted diseased site.

In the practice of the invention, a therapeutically effective amount of the hydrophilic cationic drug agent is used. In some embodiments, the hydrophilic cationic drug agent may be applied to the top-coat layer using an aqueous solution of greater than 0.01 wt % or 0.02 wt % or 0.05 wt % or 0.1 wt % or 0.2 wt % of the drug agent based on the total weight of the aqueous solution.

The implantable medical device may include devices intended for long term implant in a patient such as a stent. Durations of the device within the patient's body can be days, weeks, months or years. The implantable medical device may also include devices intended for short term entry into the patient such as a balloon catheter. Duration of the device within the patient's body may be for minutes or hours.

Methods for preparing the implantable medical device described herein comprise the steps of (i) applying a base coat layer to a substrate surface of the medical device; (ii) applying a top-coat layer of a hydrophilic polymer chemically crosslinked and covalently bonded to the base coat layer, the hydrophilic polymer consisting an anionic polyelectrolyte; and (iii) adding an amount of the hydrophilic cationic drug agent to the top-coat layer sufficient to load an effective dosage of the drug agent for the intended drug treatment.

Experimental

Cationic drug agents recited in the examples are caffeine, procaine hydrochloride, heparin sodium, chlorhexidine digluconate, 4-amino-1,8 naphthalimide dye, gentamycin hydrochloride, and lidocaine hydrochloride.

Basecoat polymers recited in the examples are:

Basecoat 1: Acrylic copolymer (butyl acrylate, butyl methacrylate and acrylic acid) emulsion with polyaziridine crosslinker, as described in U.S. Pat. No. 6,673,453 (incorporated herein by reference), and Basecoat 2: Acrylic copolymer solution of butyl acrylate, methyl methacrylate, hydroxyethyl methacrylate and monomers that promote bonding of the topcoat to the basecoat, with polyaziridine and isocyanate crosslinkers in PMA (glycol ether acetate; propylene glycol methyl ether acetate;) solvent.

Topcoat polymers recited in the examples are:

Topcoat 1: Polyelectrolyte solution comprised of hyaluronic acid and polyacrylic acid with additives that promote basecoat wetting; and Topcoat 2: Polyelectrolyte solution comprised of copolymer of acrylic acid and hydroxyethyl acrylamide with additives that promote basecoat wetting.

The cationic drug agents, top-coat and base coat compositions noted above are used in the following examples.

Figure 1:
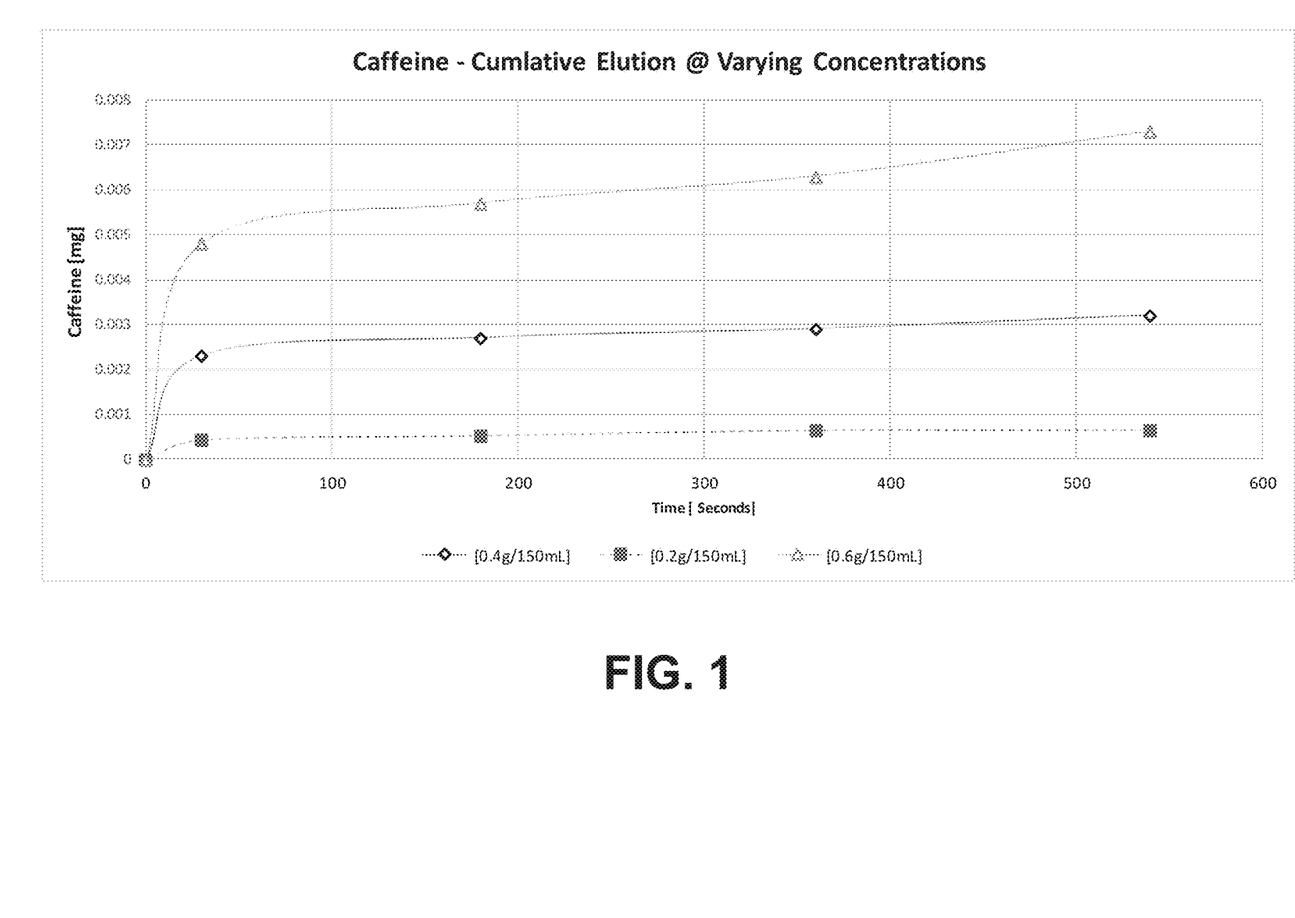
FIG. 1 shows a graphical representation of a cumulative elution of caffeine at varying concentrations in milligrams as a function of time.

Process 1: Samples of 30 centimeter long polyurethane, 80A hardness, tubes were prepared and coated with the Basecoat 2 described above. The basecoat was then dried for 20 minutes at 60° C. and dipped into Topcoat 1 solution of 150 grams (g) that had been doped with 0.2 g, 0.4 g, and 0.6 g of caffeine. The samples were cured for 120 minutes at 60° C. The fully cured sample was then soaked in a phosphate buffered saline (PBS) solution to elute the caffeine. A ultraviolet-visible UV-VIS measurement of the PBS solution was recorded at 30 seconds, 3 minutes, 6 minutes, and 9 minutes. The peak value at 270 nanometers (nm), which indicated caffeine was present, was then used to estimate the elution rate of the caffeine from the cured device as shown in FIG. 1.

Figure 2:
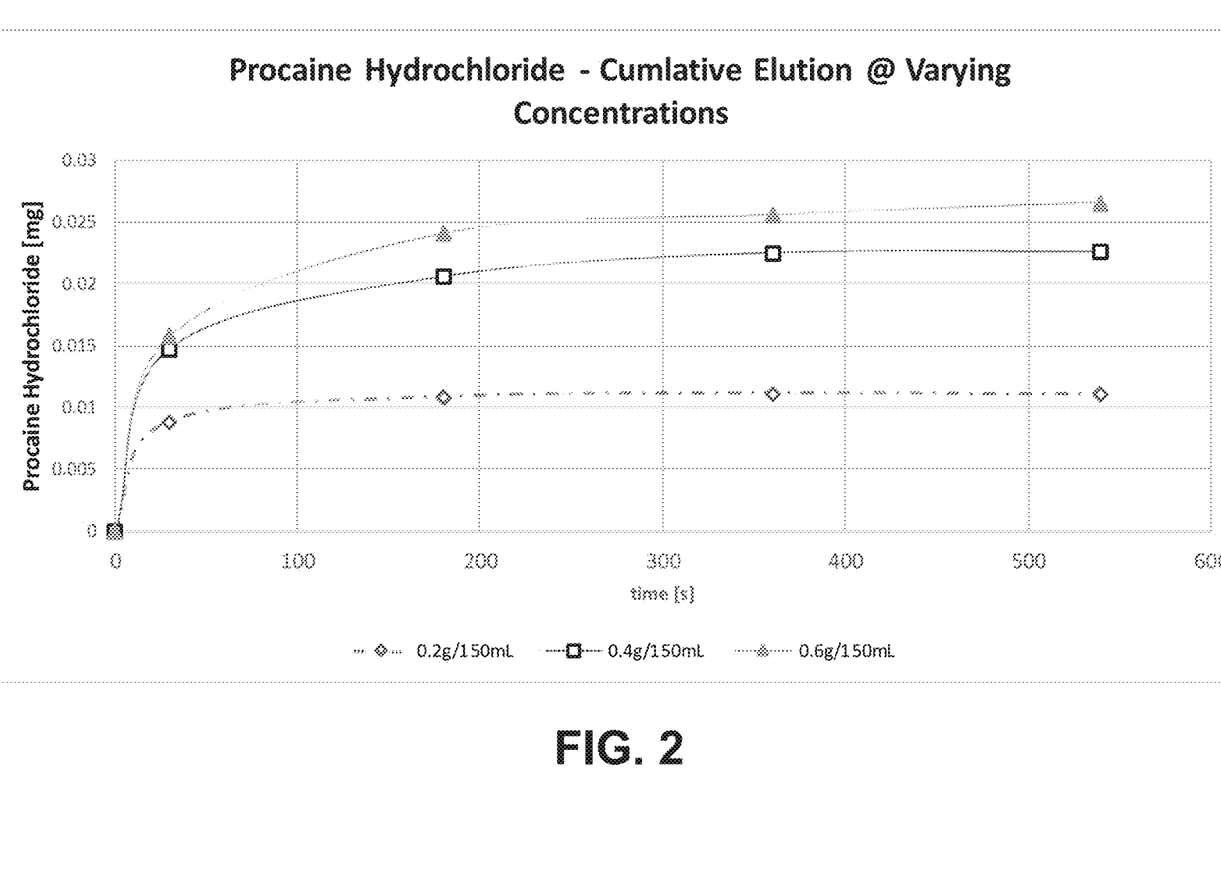
FIG. 2 shows a graphical representation of a cumulative elution of procaine hydrochloride at varying concentrations in milligrams as a function of time.

Process 2: Samples of 30 centimeter long polyurethane, 80A hardness, tubing were prepared and coated with the Basecoat 2 described above. The basecoat was then dried for 20 minutes at 60° C. and dipped into Topcoat 1 solution of 150 g that had been doped with 0.2 g, 0.4 g, and 0.6 g of Procaine Hydrochloride. The samples were cured for 120 minutes at 60° C. The fully cured sample was then soaked in a phosphate buffered saline (PBS) solution to elute the procaine hydrochloride. A UV-VIS measurement of the PBS solution was recorded at 30 seconds, 3 minutes, 6 minutes, and 9 minutes. The peak value at 290 nm, which indicated procaine hydrochloride was present, was then used to estimate the elution rate of the procaine hydrochloride from the cured device as shown in FIG. 2.

Process 3

Samples of 17-centimeter long polyurethane, 80A hardness, tubing are prepared and coated with Basecoat 1, dried for 20 minutes at 60° C. and then dipped into a 0.1% solution of the cationic drug agent and high purity water. After drying, each coated sample is then soaked in a phosphate buffered saline (PBS) solution to estimate how much of the cationic drug agent elutes from the sample.

Process 4

Samples of 17-centimeter long polyurethane, 80A hardness, tubing are prepared and coated with Basecoat 2 and Topcoat 1. The base layer is cured for 20 minutes at 60° C. and the top layer is cured for 2 hours at 60° C. After the initial curing, these samples are dipped into a 0.1% solution of the cationic drug agent and high purity water. After dipping into the cationic drug solution, the samples are cured a second time at 60° C. for one hour. After drying, each coated sample is then soaked in a PBS solution to estimate how much of the cationic drug agent elutes from the sample.

Process 5

Samples of 17-centimeter long polyurethane, 80A hardness, tubing are prepared and coated with Basecoat 2 and cured for 20 minutes at 60° C. A mixture 80 ml of Topcoat 2 and 20 ml of 0.1% solution of the cationic drug agent and high purity water is applied together as a topcoat and cured for 2 hours at 60° C. After drying, each coated sample is then soaked in a PBS solution to estimate how much of the cationic drug agent elutes from the sample.

Process 6

Samples of 17-centimeter long polyurethane, 80A hardness, tubing are prepared and coated with Basecoat 2 and Topcoat 2. The base layer is cured for 20 minutes at 60° C. and the top layer is cured for 2 hours at 60° C. After the initial curing, these samples are dipped into a 0.1% solution of the cationic drug agent and high purity water (bacterial count less than 10 colony forming units/milliliter (CFU/ml). After being dipped into the aqueous cationic agent solution, the samples are cured a second time before soaking in PBS for 60 minutes at room temperature to estimate how much of the cationic drug agent elutes from the sample.

For the following experiments, a solution of 0.3% solution of the cationic drug in high purity water is prepared as the cationic drug coating solution.

Process 7

Samples of 17-centimeter long polyurethane, 80A hardness, tubing are prepared and coated with Basecoat 2 and Topcoat 2. The base layer is cured for 20 minutes at 60° C. and the top layer is cured for 2 hours at 60° C. A final drug-loaded layer, consisting of 30 ml of the cationic drug coating solution and 70 ml of Topcoat 2, is applied by dipping the coated substrate in the drug agent solution without using a set dwell period. A final curing process of the coated, drug-loaded samples at 60° C. for about 1 hour is performed to dry the coating. After curing, each coated sample is then soaked in a PBS solution to estimate how much of the cationic drug agent elutes from the sample.

Process 8

Samples of 17-centimeter long polyurethane, 80A hardness, tubing are prepared and coated with Basecoat 2 and cured for 20 minutes at 60° C. Samples are dried for 20 minutes and a layer of Topcoat 2 is applied. This layer is cured for 2 hours and then a final layer of the cationic drug agent solution is applied and dried. After drying, each coated sample is then soaked in a phosphate buffered saline (PBS) solution to estimate how much of the cationic drug agent elutes from the sample.

Process 9

Samples of 17-centimeter long polyurethane, 80A hardness, tubing are prepared and coated with Basecoat 2 and Topcoat 1. The base layer is cured for 20 minutes and the top layer is cured for 2 hours. A final layer consisting of the cationic drug agent coating solution is applied and dried similarly to the samples in Process #8. After drying, each coated sample is then soaked in a phosphate buffered saline (PBS) solution to estimate how much of the cationic drug agent elutes from the sample. The present disclosure relates to at least the following aspects.

Aspect 1A. An implantable medical device comprising: a base coat layer having an inner and outer surface, the inner surface of the base coat layer contacting the implantable medical device; a top-coat layer of a hydrophilic polymer chemically crosslinked and covalently bonded to the outer surface of the base coat layer, the hydrophilic polymer comprising an anionic polyelectrolyte; and an amount of a hydrophilic cationic drug agent added to the top-coat layer sufficient to provide an effective dosage of the drug agent for delivery to a patient, whereby the hydrophilic cationic drug agent is initially adsorbed into the anionic polyelectrolyte of the top-coat layer and the hydrophilic cationic drug agent having a release rate after the medical device is implanted within a patient's body.

Aspect 1B. An implantable medical device comprising: a base coat layer having an inner and outer surface, the inner surface of the base coat layer contacting the implantable medical device; a top-coat layer comprising a hydrophilic polymer chemically crosslinked and covalently bonded to the outer surface of the base coat layer, the hydrophilic polymer comprising an anionic polyelectrolyte; and an amount of a hydrophilic cationic drug agent added to the top-coat layer sufficient to provide an effective dosage of the drug agent for delivery to a patient, whereby the hydrophilic cationic drug agent is initially adsorbed into the anionic polyelectrolyte of the top-coat layer and the hydrophilic cationic drug agent having a release rate after the medical device is implanted within a patient's body.

Aspect 1C. An implantable medical device comprising: a base coat layer having an inner and outer surface, the inner surface of the base coat layer contacting the implantable medical device; a top-coat layer wherein the top-coat layer is a hydrophilic polymer chemically crosslinked and covalently bonded to the outer surface of the base coat layer, the hydrophilic polymer comprising an anionic polyelectrolyte; and an amount of a hydrophilic cationic drug agent added to the top-coat layer sufficient to provide an effective dosage of the drug agent for delivery to a patient, whereby the hydrophilic cationic drug agent is initially adsorbed into the anionic polyelectrolyte of the top-coat layer and the hydrophilic cationic drug agent having a release rate after the medical device is implanted within a patient's body.

Aspect 1D. An implantable medical device consisting essentially of: a base coat layer having an inner and outer surface, the inner surface of the base coat layer contacting the implantable medical device; a top-coat layer of a hydrophilic polymer chemically crosslinked and covalently bonded to the outer surface of the base coat layer, the hydrophilic polymer comprising an anionic polyelectrolyte; and an amount of a hydrophilic cationic drug agent added to the top-coat layer sufficient to provide an effective dosage of the drug agent for delivery to a patient, whereby the hydrophilic cationic drug agent is initially adsorbed into the anionic polyelectrolyte of the top-coat layer and the hydrophilic cationic drug agent having a release rate after the medical device is implanted within a patient's body.

Aspect 2. The implantable medical device of aspect 1, wherein the anionic polyelectrolyte of the top-coat layer is selected from the group consisting of sodium hyaluronate, hyaluronic acid, hyaluronan, poly(acrylic acid) homopolymer and copolymers, sodium alginate, heparin, carboxymethyl cellulose, methacrylic acid homopolymer and copolymers, maleic anhydride copolymers, itaconic acid copolymers, 2-Acrylamido-2-methylpropane sulfonic acid copolymers, and 3-sulfopropyl acrylate copolymers.

Aspect 3. The implantable medical device of aspect 1, wherein the base coat layer comprises an acrylic polymer.

Aspect 4. The implantable medical device of aspect 1, wherein the hydrophilic cationic drug agent is selected from a group consisting of a class of water soluble, protonated amine drugs.

Aspect 5. The implantable medical device of aspect 1, wherein the hydrophilic cationic drug agent is selected from anti-infectives, antibacterial, antifungal, antiarthritics, anti-inflammatories, photoactivatable naphthalimide dyes for tissue crosslinking, anesthetics, antiarrhythmics, antiprotozoal, antineoplastic, cancer treatments drugs and imiquimod.

Aspect 6. The implantable medical device of aspect 5, wherein the anesthetics comprise one or more of Procaine HCl, Benzocain and Lidocaine HCl.

Aspect 7. The implantable medical device of aspect 5, wherein the antiarrhythmics comprises Procainamide HCl.

Aspect 8. The implantable medical device of aspect 5, wherein the antiprotozoals comprises one or more of Diminazene Aceturate and Pentamidine.

Aspect 9. The implantable medical device of aspect 5, wherein the antineoplastics comprises one or both of Improsulfan and Thiamiprine.

Aspect 10. The implantable medical device of aspect 5, wherein the cancer treatments drugs comprise one or more of Tipiracil, Ponatinib hydrochloride, Radotinib hydrochloride, Alectinib hydrochloride, Copanlisib hydrochloride, Nelarabine, Tirapazamine, Clofarabine, Fludarabine, Vandetanib, and Abemaciclib.

Aspect 11. The implantable medical device of aspect 5, wherein the anti-infectives comprise one or more of anti-bacterial, anti-viral, anti-fungal and anti-parasitic agents.

Aspect 12. The implantable medical device of aspect 11, wherein the one or more of anti-bacterial, anti-viral, anti-fungal and anti-parasitic agents aminoglycosides, cephalosporins, penicillins, chloramphenicol, isoniazid, trimethoprim and small cationic peptides or large peptides with polycationic domains.

Aspect 13. The implantable medical device of aspect 5, wherein the antibacterial, antifungal, antiarthritics, anti-inflammatories comprise streptomycin or animoglcoside.

Aspect 14. The implantable medical device of aspect 1, wherein the hydrophilic cationic drug agent comprises one or more of Imiquimod, Tetracycline, Streptomycin, Niacinamide, Clindamycine, Dapsone, Naftifine, Miconazole, Erythromycin, Terbinafine, Amitriptyline, Bisoctrizole, Benzalkonium Chloride, Chlorhexidine, Celecoxib, N,N-Dimethyl 4-aminobenzene, Diclofenac, DOXepin, Fluconazole, Gabapentin, Ketamine, Lidocaine, Benzocaine, Metronida Zole, Morphine, Nicotine, Octenidine, and Octopirox.

Aspect 15. The implantable medical device of aspect 5, wherein the hydrophilic cationic drug agent is a photoactive 4-amino substituted 1,8-naphthalamide compound.

Aspect 16. The implantable medical device of aspect 1, wherein the amount of drug agent is sufficient for delivery to a targeted diseased site.

Aspect 17. A method for preparing an implantable medical device intended to provide an intracorporeal drug treatment at a targeted diseased site using a hydrophilic cationic drug agent, comprising the steps of: applying a base coat layer to a substrate surface of the medical device; applying a top-coat layer of a hydrophilic polymer chemically crosslinked and covalently bonded to the base coat layer, the hydrophilic polymer consisting an anionic polyelectrolyte; and adding an amount of the hydrophilic cationic drug agent to the top-coat layer sufficient to load an effective dosage of the drug agent for the intended drug treatment.

Aspect 18. The method according to aspect 17, wherein the anionic polyelectrolyte of the top-coat layer is selected from the group consisting of sodium hyaluronate, hyaluronic acid, hyaluronan, poly(acrylic acid) homopolymer and copolymers, sodium alginate, heparin, carboxymethyl cellulose, methacrylic acid homopolymer and copolymers, maleic anhydride copolymers, itaconic acid copolymers, 2-acrylamido-2-methylpropane sulfonic acid copolymers, and 3-sulfopropyl acrylate copolymers.

Aspect 19. The method according to aspect 17, wherein the hydrophilic cationic drug agent is selected from a group consisting of a class of water soluble, protonated amine drugs.

Aspect 20. The method of aspect 17, wherein the hydrophilic cationic drug agent is selected from anti-infectives, antibacterial, antifungal, antiarthritics, anti-inflammatories, photoactivatable naphthalimide dyes for tissue crosslinking, anesthetics, antiarrhythmics, antiprotozoal, antineoplastic, cancer treatments drugs and imiquimod.

Aspect 21. The method of aspect 20, wherein the anesthetics comprise one or more of Procaine HCl, Benzocain and Lidocaine HCl.

Aspect 22. The method of aspect 20, wherein the antiarrhythmics comprises Procainamide HCl.

Aspect 23. The method of aspect 20, wherein the antiprotozoal, comprises one or more of Diminazene Aceturate and Pentamidine.

Aspect 24. The method of aspect 20, wherein the antineoplastic comprises one or both of Improsulfan and Thiamiprine.

Aspect 25. The method of aspect 20, wherein the cancer treatments drugs comprise one or more of Tipiracil, Ponatinib hydrochloride, Radotinib hydrochloride, Alectinib hydrochloride, Copanlisib hydrochloride, Nelarabine, Tirapazamine, Clofarabine, Fludarabine, Vandetanib, and Abemaciclib.

Aspect 26. The method of aspect 20, wherein the anti-infectives comprise one or more of anti-bacterial, anti-viral, anti-fungal and anti-parasitic agents.

Aspect 27. The method of aspect 26, wherein the one or more of anti-bacterial, anti-viral, anti-fungal and anti-parasitic agents comprise aminoglycosides, cephalosporins, penicillins, chloramphenicol, isoniazid, trimethoprim and small cationic peptides or large peptides with polycationic domains.

Aspect 28. The method of aspect 20, wherein the antibacterial, antifungal, antiarthritics, anti-inflammatories comprise streptomycin or animoglcoside.

Aspect 29. The method of aspect 17, wherein the hydrophilic cationic drug agent comprises one or more of Imiquimod, Tetracycline, Streptomycin, Niacinamide, Clindamycine, Dapsone, Naftifine, Miconazole, Erythromycin, Terbinafine, Amitriptyline, Bisoctrizole, Benzalkonium Chloride, Chlorhexidine, Celecoxib, N,N-Dimethyl 4-aminobenzene, Diclofenac, DOXepin, Fluconazole, Gabapentin, Ketamine, Lidocaine, Benzocaine, Metronida Zole, Morphine, Nicotine, Octenidine, and Octopirox.

Aspect 30. The method of aspect 20, wherein the hydrophilic cationic drug agent is a photoactive 4-amino substituted 1,8-naphthalamide compound.

Aspect 31. The method of aspect 17, wherein the base coat layer comprises an acrylic polymer.

Throughout this specification, words are to be afforded their normal meaning, as would be understood by those skilled in the relevant art, unless otherwise indicated. However, so as to avoid misunderstanding, the meanings of certain terms will be specifically defined or clarified.

In the present disclosure the singular forms "a," "an," and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about," it will be understood that the particular value forms another embodiment. In general, use of the term "about" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about." In other cases, the gradations used in a series of values may be used to determine the intended range available to the term "about" for each value.

As used herein, the terms "about" and "at or about" mean that the amount or value in question can be the designated value, approximately the designated value, or about the same as the designated value. As used herein, the terms "about" and "at or about" mean that the amount or value in question can be the value designated some other value approximately or about the same. It is generally understood, as used herein, that it is the nominal value indicated ±10% or ±5% variation unless otherwise indicated or inferred. The term is intended to convey that similar values promote equivalent results or effects recited in the claims. That is, it is understood that amounts, sizes, formulations, parameters, and other quantities and characteristics are not and need not be exact, but can be approximate and/or larger or smaller, as desired, reflecting tolerances, conversion factors, rounding off, measurement error and the like, and other factors known to those of skill in the art. It is understood that where "about" is used before a quantitative value, the parameter also includes the specific quantitative value itself, unless specifically stated otherwise.

Where present, all ranges are inclusive and combinable. That is, references to values stated in ranges include every value within that range including the endpoint values.

When a list is presented, unless stated otherwise, it is to be understood that each individual element of that list and every combination of that list is to be interpreted as a separate embodiment. For example, a list of embodiments presented as "A, B, or C" is to be interpreted as including the embodiments, "A," "B," "C," "A and B," "A and C," "B and C," or "A, B, and C."

It is to be appreciated that certain features of the invention which are, for clarity, described herein in the context of separate embodiments, may also be provided in combination in a single embodiment. That is, unless obviously incompatible or specifically excluded, each individual embodiment is deemed to be combinable with any other possible embodiment(s) and such a combination is considered to be another embodiment. Conversely, various features of the invention that are, for brevity, described in the context of a single embodiment, may also be provided separately or in any sub-combination. Further, while an embodiment may be described as part of a series of steps or part of a more general structure, each said step or part may also be considered an independent embodiment in itself.

As used herein, the terms "article" and "substrate" are not limited to any shape or size, as it may be a layer of material, multiple layers or a block having at least one surface of which is modified by a coating composition described herein.

The phrase "implantable device" may include long and short term items that can placed in a patient's body. These devices include stents and catheter balloons. Some devices are constructed of plastics and/or metals that were never intended to invade and sometimes reside for prolonged periods in the human body. These plastics and metals present surfaces that bear little or no resemblance to those of human organs, which are generally hydrophilic, slippery and biocompatible. In addition to delivery of drug agents, the coatings of the instant invention provide improved compatibility with the patient's body. Equally important for devices that must be inserted and moved through body tissues is their lubricity. Most metals and plastics have poor lubricity against body tissues, which results in mechanical abrasion and discomfort when the device is passed over the tissue. The coatings of the instant invention, in addition to delivery of the drug agent, improves lubricity of the device.

By cationic drug is meant any drug that, in water or aqueous media, either is cationic by its chemical nature or is protonated by water to become cationic.

As used herein the term "hydrophobic" is characterized by the lack of solubility of the non-crosslinked polymer in water.

The term "hydrophilic" refers to a substrate surface made of a polymer where the uncured or non-crosslinked polymer is soluble in water or in a water alcohol solution that is more than 50% water.

Unless otherwise specified, all molecular weights are weight-average molecular weights (Mw).

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37

C.F.R. § 1.72(b), to allow the reader to quickly ascertain the nature of the technical disclosure. It is submitted with the understanding that it will not be used to interpret or limit the scope or meaning of the claims. The following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed:

1. An implantable medical device comprising:
   a base coat layer having an inner and outer surface, the inner surface of the base coat layer contacting the implantable medical device;
   a top-coat layer of a hydrophilic polymer chemically crosslinked and covalently bonded to the outer surface of the base coat layer, the hydrophilic polymer comprising an anionic polyelectrolyte, wherein the hydrophilic polymer comprises a poly(acrylic acid) copolymer; and
   an amount of a hydrophilic cationic drug agent added to the top-coat layer sufficient to provide an effective dosage of the drug agent for delivery to a patient,
   whereby the hydrophilic cationic drug agent is initially adsorbed into the anionic polyelectrolyte of the top-coat layer and the hydrophilic cationic drug agent having a release rate after the medical device is implanted within a patient's body,
   wherein the hydrophilic cationic drug agent is selected from a group consisting of a class of water soluble, protonated amine drugs.

2. The implantable medical device of claim 1, wherein the poly(acrylic acid) copolymer comprises a copolymer of polyacrylic acid and hyaluronic acid or hydroxyethyl acrylamide.

3. The implantable medical device of claim 1, wherein the base coat layer comprises an acrylic polymer.

4. The implantable medical device of claim 1, wherein the hydrophilic cationic drug agent is selected from anti-infectives, antibacterial, antifungal, antiarthritics, anti-inflammatories, photoactivatable naphthalimide dyes for tissue crosslinking, anesthetics, antiarrhythmics, antiprotozoal, antineoplastic, cancer treatments drugs and imiquimod.

5. The implantable medical device of claim 4, wherein the anesthetics comprise one or more of Procaine HCl, Benzocaine and Lidocaine HCl.

6. The implantable medical device of claim 4, wherein the antiarrhythmics comprises Procainamide HCl.

7. The implantable medical device of claim 4, wherein the antiprotozoals comprises one or more of Diminazene Aceturate and Pentamidine.

8. The implantable medical device of claim 4, wherein the antineoplastics comprises one or both of Improsulfan and Thiamiprine.

9. The implantable medical device of claim 4, wherein the cancer treatments drugs comprise one or more of Tipiracil, Ponatinib hydrochloride Radotinib hydrochloride, Alectinib hydrochloride, Copanlisib hydrochloride, Nelarabine, Tirapazamine Clofarabine, Fludarabine, Vandetanib, and Abemaciclib.

10. The implantable medical device of claim 4, wherein the anti-infectives comprise one or more of anti-bacterial, anti-viral, anti-fungal and anti-parasitic agents.

11. The implantable medical device of claim 10, wherein the one or more of anti-bacterial, anti-viral, anti-fungal and anti-parasitic agents comprises aminoglycosides, cephalosporins, penicillins, chloramphenicol, isoniazid, trimethoprim and small cationic peptides or large peptides with polycationic domains.

12. The implantable medical device of claim 4, wherein the antibacterial antifungal, antiarthritics, anti-inflammatories comprise streptomycin or aminoglycoside.

13. The implantable medical device of claim 4, wherein the hydrophilic cationic drug agent is a photoactive 4-amino substituted 1,8-naphthalimide compound.

14. The implantable medical device of claim 1, wherein the hydrophilic cationic drug agent comprises one or more of Imiquimod, Tetracycline, Streptomycin, Niacinamide, Clindamycin, Dapsone, Naftifine, Miconazole, Erythromycin, Terbinafine, Amitriptyline, Bisoctrizole, Benzalkonium Chloride, Chlorhexidine, Celecoxib, N,N-Dimethyl 4-aminobenzene, Diclofenac, Doxepin, Fluconazole, Gabapentin, Ketamine, Lidocaine, Benzocaine, Metronidazole, Morphine, Nicotine, Octenidine, and Octopirox.

15. The implantable medical device of claim 1, wherein the amount of drug agent is sufficient for delivery to a targeted diseased site.

16. A method for preparing an implantable medical device intended to provide an intracorporeal drug treatment at a targeted diseased site using a hydrophilic cationic drug agent, comprising the steps of:
   applying a base coat layer to a substrate surface of the medical device;
   applying a top-coat layer of a hydrophilic polymer chemically crosslinked and covalently bonded to the base coat layer, the hydrophilic polymer consisting an anionic polyelectrolyte; and
   adding an amount of the hydrophilic cationic drug agent to the top-coat layer sufficient to load an effective dosage of the drug agent for the intended drug treatment,
   wherein the hydrophilic cationic drug agent is selected from a group consisting of a class of water soluble, protonated amine drugs.

17. The method according to claim 16, wherein the anionic polyelectrolyte of the top-coat layer is selected from the group consisting of sodium hyaluronate, hyaluronic acid, hyaluronan, poly(acrylic acid) homopolymer and copolymers, sodium alginate, heparin, carboxymethyl cellulose, methacrylic acid homopolymer and copolymers, maleic anhydride copolymers, itaconic acid copolymers, 2-acrylamido-2-methylpropane sulfonic acid copolymers, and 3-sulfopropyl acrylate copolymers.

18. The method according to claim 16, wherein the hydrophilic cationic drug agent is selected from a group consisting of a class of water soluble, protonated amine drugs.

19. The method of claim 16, wherein the hydrophilic cationic drug agent is selected from anti-infectives, antibacterial, antifungal, antiarthritics, anti-inflammatories, photoactivatable naphthalimide dyes for tissue crosslinking, anesthetics, antiarrhythmics, antiprotozoal, antineoplastic, cancer treatments drugs and imiquimod.

20. The method of claim 19, wherein the anesthetics comprise one or more of Procaine HCl, Benzocaine and Lidocaine HCl.

21. The method of claim 19, wherein the antiarrhythmics comprises Procainamide HCl.

22. The method of claim 19, wherein the antiprotozoal, comprises one or more of Diminazene Aceturate and Pentamidine.

23. The method of claim 19, wherein the antineoplastic comprises one or both of Improsulfan and Thiamiprine.

24. The method of claim 19, wherein the cancer treatments drugs comprise one or more of Tipiracil, Ponatinib hydrochloride, Radotinib hydrochloride, Alectinib hydrochloride, Copanlisib hydrochloride, Nelarabine, Tirapazamine, Clofarabine, Fludarabine, Vandetanib, and Abemaciclib.

25. The method of claim 19, wherein the anti-infectives comprise one or more of anti-bacterial, anti-viral, anti-fungal and anti-parasitic agents.

26. The method of claim 25, wherein the one or more of anti-bacterial, anti-viral, anti-fungal and anti-parasitic agents comprise aminoglycosides, cephalosporins, penicillins, chloramphenicol, isoniazid, trimethoprim and small cationic peptides or large peptides with polycationic domains.

27. The method of claim 19, wherein the antibacterial, antifungal, antiarthritics, anti-inflammatories comprise streptomycin or aminoglycoside.

28. The method of claim 19, wherein the hydrophilic cationic drug agent is a photoactive 4-amino substituted 1,8-naphthalimide compound.

29. The method of claim 16, wherein the hydrophilic cationic drug agent comprises one or more of Imiquimod, Tetracycline, Streptomycin, Niacinamide, Clindamycin, Dapsone, Naftifine, Miconazole, Erythromycin, Terbinafine, Amitriptyline, Bisoctrizole, Benzalkonium Chloride, Chlorhexidine, Celecoxib, N,N-Dimethyl 4-aminobenzene, Diclofenac, Doxepin, Fluconazole, Gabapentin, Ketamine, Lidocaine, Benzocaine, Metronidazole, Morphine, Nicotine, Octenidine, and Octopirox.

30. The method of claim 16, wherein the base coat layer comprises an acrylic polymer.

\* \* \* \* \*